United States Patent [19]
Hitomi et al.

[11] Patent Number: 5,624,967
[45] Date of Patent: Apr. 29, 1997

[54] WATER-ABSORBING RESIN AND PROCESS FOR PRODUCING SAME

[75] Inventors: Kazuhisa Hitomi; Takumi Hatsuda, both of Hyogo; Tadao Shimomura, Osaka, all of Japan

[73] Assignee: Nippon Shokubai Co., Ltd., Japan

[21] Appl. No.: 473,517

[22] Filed: Jun. 7, 1995

[51] Int. Cl.$^6$ .................................................. C08J 9/28
[52] U.S. Cl. .................. 521/64; 521/63; 524/845; 524/846; 604/369
[58] Field of Search ................ 521/64, 63; 524/845, 524/846; 604/369

[56] References Cited

U.S. PATENT DOCUMENTS

| | | |
|---|---|---|
| Re. 32,649 | 4/1988 | Brandt et al. . |
| 4,985,514 | 1/1991 | Kimura et al. . |
| 5,147,343 | 9/1992 | Kellenberger . |
| 5,213,893 | 5/1993 | Kobayashi et al. . |

FOREIGN PATENT DOCUMENTS

| | | | |
|---|---|---|---|
| 0280541 | 8/1988 | European Pat. Off. | ...... C08F 220/06 |
| 0315185 | 5/1989 | European Pat. Off. | ...... C08F 220/04 |
| 0347241 | 12/1989 | European Pat. Off. | ...... C08F 220/06 |
| 0388254 | 9/1990 | European Pat. Off. | ...... C08F 220/06 |
| 2126591 | 3/1984 | United Kingdom | ............... C08J 3/24 |

*Primary Examiner*—Morton Foelak
*Attorney, Agent, or Firm*—Dominik & Stein

[57] ABSTRACT

A process for producing a water-absorbing resin, which comprises polymerizing (D) an aqueous solution comprising (A) at least one monomer component selected from the group consisting of an unsaturated carboxylic acid and salts thereof; (B) a compound having two or more unsaturated groups in a molecule; and (C) a compound having two or more functional groups which are capable of reacting with carboxyl groups in a molecule, the polymerization being conducted in such a manner that the following conditions (a) to (c) are simultaneously satisfied: (a) the molar ratio (B)/(C) being in the range of from $2\times10^{-3}$ to 300, (b) the polymerization being initiated by a redox polymerization initiator, and (c) the maximum reaction temperature being in the range of from 60° to 100° C, and a water-absorbing resin having a degree of reduction in absorption magnification of from 1 to 16, and n absorption magnification under pressure of from 20 to 40.

19 Claims, 1 Drawing Sheet

FIG. 1

WATER-ABSORBING RESIN AND PROCESS FOR PRODUCING SAME

FIELD OF THE INVENTION

The present invention relates to a process for producing a water-absorbing resin, and more specifically, relates to a process for producing a water-absorbing resin that is excellent in absorbing properties and has a reduced amount of water-soluble content. The present invention also relates to a water-absorbing resin, and more specifically it relates to a water-absorbing resin that has a reduced amount of water-soluble content, a high salt resistance, and excellent absorbing properties under pressure. The present invention also relates to a water-absorbing article, and more specifically it relates to a water-absorbing article containing a water-absorbing resin that has a reduced amount of water-soluble content, a high salt resistance, and excellent absorbing properties under pressure.

BACKGROUND OF THE INVENTION

Water-absorbing resins have been used in various absorbing articles. Such article include diapers, sanitary goods, soil water-retaining agent, freshness-maintaining agents, dew condensation preventing agents, sealing materials, etc.

Various water-absorbing resins and processes for producing them have been proposed. Examples of the known water-absorbing resins include a hydrolyzed product of a starch-acrylonitrile graft copolymer (as described in JP-B-49-43395), a partially neutralized material of a starch-acrylic acid graft copolymer (as described in JP-B-53-46199), a saponified material of a acrylic acid ester-vinyl acetate copolymer (as described in JP-B-53-13495), a crosslinked material of a partially neutralized acrylic acid (as described in JP-B-58-35605), a modified material of a crosslinked polyvinyl alcohol (as described in JP-A-54-20093), etc. (The term "JP-B" as used herein means an examined Japanese patent publication, and the term "JP-A" as used herein means an unexamined published Japanese patent application.)

The above-described conventional water-absorbing resins contain a certain amount of water-soluble content. The presence of the water-soluble content sometimes is not desirable in the aspect of both the performance and the safety of the water-absorbing resin. For example, when the water-absorbing resin is in contact with a liquid to be absorbed to form a hydrogel structure whereby the water-soluble content is extracted into the liquid to be absorbed, not only the absorbing properties of the resin are reduced in proportion to the extracted water-soluble content, but also deterioration of the water-absorbing resin is accelerated. When a large amount of the water-soluble content is in contact with a human body, etc., such a water-soluble content sometimes is not desirable from the viewpoint of safety as it gives unpleasant slimy feeling, etc.

Processes for producing water-absorbing resins having a small amount of water-soluble content have been proposed. Examples of such processes include a process comprising polymerizing a monomer containing both a polymerizable unsaturated group and a free acid group, followed by neutralization (as described in JP-A-62-54751), a process comprising polymerizing a low-neutralized monomer, followed by neutralization (as described in JP-A-1-144404), a process comprising irradiating a water-absorbing resin with an ultraviolet ray in the presence of a radical scavenger (as described in JP-A-4-120112), a process comprising adding a reducing substance and a radical scavenger to a water-absorbing resin (as described in JP-A-4-120111), etc.

The above-described processes each includes a new unit operation which is required in production steps. For example, in the processes of JP-A-62-54751 and JP-A-4-144404, a neutralization step is required after the polymerization. In the processes of JP-A-4-120112 and JP-A-4-120111, a step for mixing an additive with the water-absorbing resin and a step for irradiating the water-absorbing resin with an ultraviolet ray are required. In the step for neutralization of the water-absorbing resin after polymerization, and the step for mixing additives with the water-absorbing resin after polymerization, a uniform neutralization or mixing is difficult and may cause a decrease in the productivity.

It is generally known that the amount of water-soluble content can be reduced by increasing the amount of a crosslinking agent used. However, as a result of the use of an increased amount of a crosslinking agent, the absorbing properties of the water-absorbing resin decreases.

Water-absorbing resins having a small amount of water-soluble content have been known. For example, in a process for producing a water-absorbing resin by adiabatic polymerization (as described in JP-B-1-31531), a polymer gel is treated with water and a methanol solution. In this production process, a water/methanol treatment is required and therefore the productivity decreases. Further, it is probable that methanol remains in the resulting resin and, hence, the process is not desirable from the standpoint of safety.

Water-absorbing resins sometimes required to have salt resistance. For example, the absorbing properties change depending on the kind of solutions to be absorbed and depending on the lapse of time.

The water-absorbing resin containing an electrolytic structure such as the partially neutralized acrylic acid described above generally has poor salt resistance. If such a water-absorbing resin is used as a diaper, the absorbing properties are changed due to the change in concentration of salts from electrolytes in urine and the lapse of time, resulting in fluctuation of product quality.

It is known that nonionic water-absorbing resins and sulfonic group-containing water-absorbing resins are excellent in absorbing properties to electrolytic solutions. Examples thereof include the water-absorbing resin contained in the water-swellable waterproofing material (as described in JP-A-62-259846), the water-absorbing resin contained in the waterproofing material for cables (as described in JP-A-4-363383), and the waterproofing material for optical and electric cables (as described in JP-B-5-4764). However, these water-absorbing resins have low gel strength, resulting in deteriorated absorbing properties under pressure.

Water-absorbing resins having high absorbing properties under pressure have been known. For example, a water-absorbing resin having high absorbing properties under pressure is used in the absorbing article containing hydrogel having high absorption capability under pressure (as described in U.S. Pat. No. 5,147,343).

Processes for producing a water-absorbing resin having high absorbing properties under pressure also have been known. Examples thereof include a process for producing powdery polymer with selecting surfactant (as described in French Patent 8,611,742), a process for producing a water-absorbing resin by a high-concentration polymerization (as described in JP-A-63-275607), a process for producing a water-absorbing resin by forced heating (as described in JP-A-63-275608), and a process for producing water-absorbing resin by mixing a second crosslinking agent, followed by subjecting heating treatment (as described in JP-A-6-184320). However, these water-absorbing resins having high absorbing properties under pressure do not have high salt resistance.

The present invention is directed to solution of the above-described problems.

SUMMARY OF THE INVENTION

An object of the present invention is to provide a process for producing a water-absorbing resin having satisfactory absorbing properties and having a small amount of water-soluble content.

Another object of the present invention is to provide a process for producing a water-absorbing resin having a markedly small amount of water-soluble content and high safety.

Further object of the present invention is to provide an expedient and highly productive process for producing a water-absorbing resin having satisfactory absorbing properties and a small amount of water-soluble content.

Still further object of the present invention is to provide a water-absorbing resin having a small amount of water-soluble content, high salt resistance, and excellent absorbing properties under pressure.

Still further object of the present invention is to provide a water-absorbing article containing a water-absorbing resin having a small amount of water-soluble content, high salt resistance, and excellent absorbing properties under pressure.

Still further object of the present invention is to provide a water-absorbing article having a reduced change in absorbing properties after absorption, which has been a problem in water-absorbing articles containing conventional water-absorbing resins.

The present invention relates to a process for producing a water-absorbing resin, which comprises polymerizing (D) an aqueous solution comprising (A) at least one monomer component selected from the group consisting of an unsaturated carboxylic acid and salts thereof; (B) a compound having two or more unsaturated groups in a molecule; and (C) a compound having two or more functional groups which are capable of reacting with carboxyl groups in a molecule,
the polymerization being conducted in such a manner that the following conditions (a) to (c) are simultaneously satisfied:

(a) the molar ratio (B)/(C) being in the range of from $2 \times 10^{-3}$ to 300, (b) the polymerization being initiated by a redox polymerization initiator, and (c) the maximum reaction temperature being in the range of from 60° to 100° C.

In the process according to the present invention, it is preferred that the following conditions (d) to (f) are simultaneously satisfied:

(d) the molar ratio (B)/(C) being in the range of from 0.01 to 30, (e) the molar ratio (B)/(A) being in the range of from $1 \times 10^{-4}$ to $3 \times 10^{-3}$, and (f) the molar ratio (C)/(A) being in the range of from $1 \times 10^{-4}$ to $1 \times 10^{-2}$.

It is also preferred that the process according to the present invention further comprises drying after the polymerization.

The present invention also relates to a water-absorbing resin having a degree of reduction in absorption magnification of from 1 to 16, and an absorption magnification under pressure of from 20 to 40.

The present invention further relates to a water-absorbing article comprising the above water-absorbing resins, or the above water-absorbing resins which are produced by the above processes.

DETAILED DESCRIPTION OF THE INVENTION

The "degree of reduction in absorption magnification" as used herein means the value measured according to the following method:

E (g) (about 0.2 g) of a water-absorbing resin to be measured is placed uniformly in a bag made of nonwoven cloth (40×150 mm), and immersed in an artificial urine I (an aqueous solution containing 1.9% of urea, 0.8% of sodium chloride, 0.1% of magnesium sulfate, and 0.1% of calcium chloride) at 25° C. for a prescribed period of time. After the bag is taken out from the artificial urine I, the artificial urine I is naturally drained for 5 second in the air and for further 10 seconds on 24 sheets of toilet paper each having a rectangular form of 5.0 cm×5.7 cm, and the weight (F (g)) of the bag containing the water-absorbing resin is measured. The same procedures as above are conducted by using the same nonwoven cloth bag but using no water-absorbing resin, and the weight (G (g)) of the bag is measured. The absorption magnification at the prescribed period of time is calculated by the following equation:

$$\text{Absorption magnification } (g/g) = (F(g) - G(g))/E(g)$$

The degree of reduction in absorption magnification is calculated by the following equation:

$$\text{Degree of reduction in absorption magnification } (g/g) = \text{Absorption magnification after 10 minutes } (g/g) - \text{Absorption magnification after 3 hours } (g/g)$$

Figure 1:
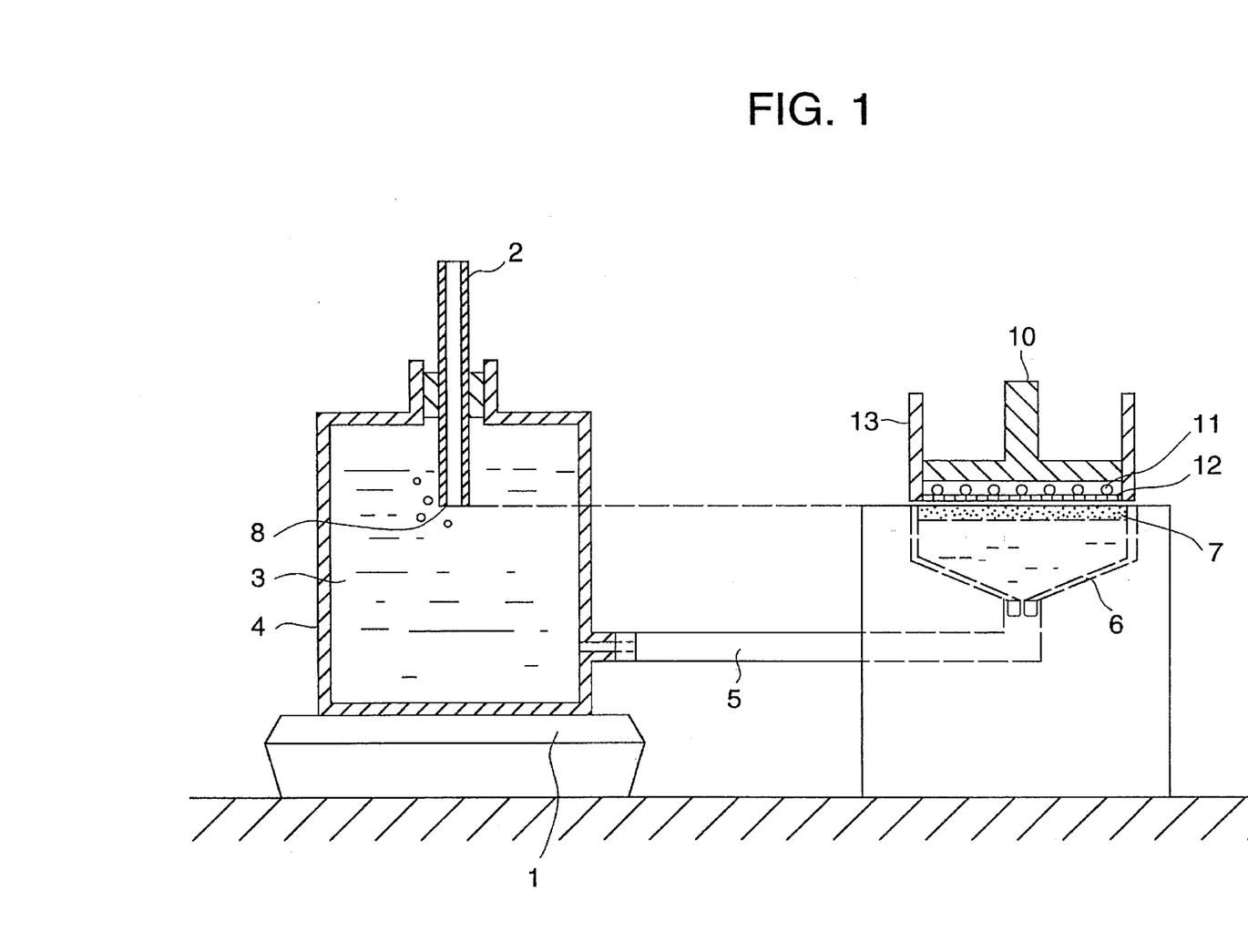
FIG. 1 shows a schematic cross section of an apparatus for measuring an absorption magnification under pressure of a water-absorbing resin.

The "absorption magnification under pressure" as used herein means a value measured according to the following method by using an apparatus shown in FIG. 1:

An artificial urine II 3 (an aqueous solution containing 2.0% of potassium chloride, 2.0% of anhydrous sodium sulfate, 0.85% of ammonium dihydrogenphosphate, 0.15% of diammonium hydrogenphosphate, 0.25% of potassium chloride dihydrate, and 0.5% of magnesium chloride hexahydrate) at 25° C. is placed in a vessel 4 equipped with an air inlet pipe 2, which is placed on a balance 1. The interior of the vessel 4 is connected to a reverse funnel 6 through a connecting pipe 5. A glass filter 7 is fixed at the top of the reverse funnel 6, while the top end of the glass filter 7 and the bottom end 8 of the air inlet pipe 2 are placed at the same height. A cylinder 13 (inner diameter: 6.0 cm) having a stainless steel mesh bottom 12 containing a water-absorbing absorbing resin 11 (0.9 g) having placed thereon a weight 10 (pressure: 0.70 psi) is placed on the glass filter 7. The weight of the artificial urine II 3 that are absorbed by the water-absorbing resin 11 after 60 minutes is divided by 0.9 to result absorption magnification under pressure (g/g).

The present invention relates to a process for producing a water-absorbing resin.

Examples of the unsaturated carboxylic acid used as the monomer component (A) in the present invention includes (meth)acrylic acid, crotonic acid, itaconic acid, maleic acid, fumaric acid, citraconic acid, etc., and one or more of these acids can be used. The use of acrylic acid is more preferred.

The term "(meth)acrylic" and the like used herein means "acrylic or methacrylic" and the like.

Examples of the salt of unsaturated carboxylic acid used as the monomer component (A) in the present invention includes an alkali metal salt, an ammonium salt and a substituted ammonium salt, etc., and one or more of these salts can be used. The use of a sodium salt of acrylic acid as a salt of unsaturated carboxylic acid salt is more preferred.

The above unsaturated carboxylic acid and salts thereof may be used singly or in combination of two or more of them.

There is no particular limitation in the amount ratio between the unsaturated carboxylic acid and the salt of unsaturated carboxylic acid for the monomer component (A), but it is preferred that the unsaturated carboxylic acid is neutralized in the range of from 30 to 90 mol%, and particularly preferably from 60 to 80 mol%.

The compound (B) having two or more unsaturated groups in a molecule used in the present invention is not particularly limited as long as it has two or more unsaturated groups in a molecule. Examples thereof include ethylene glycol di(meth)acrylate, diethylene glycol di(meth)acrylate, triethylene glycol di(meth)acrylate, propylene glycol di(meth)acrylate, polyethylene glycol di(meth)acrylate, trimethylolpropane di(meth)acrylate, trimethylolpropane tri(meth)acrylate, pentaerythritol di(meth)acrylate, pentaerythritol tri(meth)acrylate, pentaerythritol tetra(meth)acrylate, N,N-methylenebis(meth)acrylamide, triallyl isocyanurate, trimethylolpropane di(meth)allyl ether, triallylamine, tetraallyloxyethane, and glycerolpropoxy triacrylate. One or more of these compounds can be used by appropriately selecting the compounds by taking solubility and reactivity of the compounds into consideration. It is preferred to use polyethylene glycol di(meth)acrylate or trimethylolpropane tri(meth)acrylate as the compound (B).

The compound (B) having two or more unsaturated groups in a molecule used in the present invention is preferably used at a molar ratio (B)/(A) in the range of from $1\times10^{-4}$ to $3\times10^{-3}$.

An example of the process for producing a water-absorbing resin with high productivity is a process for polymerization while finely dividing the hydrogel (as described in JP-B-2-19122). When the molar ratio (B)/(A) is below $1\times10^{-4}$ the strength of a hydrogel at an early stage of the polymerization, specifically, at a stage until reaching the maximum reaction temperature, sometimes may not be sufficient to finely divide the hydrogel, even if these compounds are used together with the compound (C). When the molar ratio (B)/(A) is higher than $3\times10^{-3}$, the absorbing properties of the resulting resin may sometimes decreases to an undesirable level. The molar ratio (B)/(A) is more preferably in the range of from $5\times10^{-4}$ to $2.5\times10^{-3}$.

Examples of the compound (C) having two or more functional groups capable of reacting with carboxyl groups in a molecule include compounds having two or more epoxyl groups in a molecule such as ethylene glycol diglycidyl ether, polyethylene glycol diglycidyl ether, polypropylene glycol diglycidyl ether, neopentyl glycol diglycidyl ether, 1,6-hexanediol diglycidyl ether, glycerin triglycidyl ether and trimethylolpropane triglycidyl ether; compounds having two or more halogen groups and epoxyl groups in a molecule such as epichlorohydrin and α-methylepichlorohydrin; compounds having two or more isocyanate group such as 2,4-trilenediisocyanate and hexamethylene diisocyanate; compounds having two or more aziridine groups in a molecule such as trimethylolpropanetri (3-(1-aziridinyl)propionate) and diphenylmethane-bis-4,4'-N,N'-diethyleneurea; and compounds having two or more aziridinium salts in a molecule such as polyamide polyamine epihalohydrine adducts. These compounds can be used singly or in combination of two or more of them, with the solubility and the reactivity being taken into consideration. Among these compounds, the compound having two or more epoxyl groups in a molecule is particularly preferred as the compound (C).

The compound (C) having two or more functional groups in a molecule which is capable of reacting with carboxyl groups is preferably used at a molar ratio (C)/(A) in the range of from $5\times10^{-5}$ to $1\times10^{-2}$.

When the molar ratio (C)/(A) is below $5\times10^{-5}$, the resulting effect sometimes may be unsatisfactory, even when the compound (B) is used together. When the ratio is higher than $1\times10^{-2}$, the absorption properties of the produced water-absorbing resin tend to become low and thus may not be suitable for use in industry. The molar ratio (C)/(A) is more preferably in the range of from $1\times10^{-4}$ to $1\times10^{-2}$.

It is necessary that the molar ratio of the compound (B) to the compound (C), (B)/(C), used in the present invention is in the range of from $2\times10^{-3}$ to 300.

When the molar ratio (B)/(C) is below $2\times10^{-3}$, the strength of a hydrogel at an early stage of the polymerization, specifically, until reaching the maximum reaction temperature may be insufficient to finely divide the hydrogel. When the molar ratio (B)/(C) is more than 300, an effect obtainable by using the compound (C) and the compound (B) together may not be exhibited. The molar ratio (B)/(C) is preferably in the range of from 0.01 to 100, more preferably in the range of from 0.01 to 30.

In the present invention, it is necessary to use a redox polymerization initiator. If the redox polymerization initiator is not used, the maximum reaction temperature becomes too high since the polymerization reaction is difficult to control, and the amount of a water-soluble content in the resulting water-absorbing resin increases. Also, an introduction time until the reaction starts becomes too long whereby productivity may decrease.

Oxidizing agents of the redox polymerization initiator used in the present invention include water-soluble oxidizing agents. Examples of the water-soluble oxidizing agents include a peroxide such as hydrogen peroxide, benzoyl peroxide, cumene hydroperoxide, etc.; an alkali metal persulfate such as potassium persulfate, sodium persulfate, etc.; ammonium persulfate, alkyl hydroperoxides, etc. These oxidizing agents may be used singly or in combination of two or more of them.

The oxidizing agent is generally used in an amount of from 0.000001 to 3 g, preferably from 0.00001 to 1 g, and more preferably from 0.00001 to 0.5 g, per mol of the monomer component (A).

Examples of reducing agents of the redox polymerization initiator used in the present invention include an alkali metal sulfite, an alkali metal bisulfite, ammonium sulfite, ammonium bisulfite, ascorbic acid, erythorbic acid, etc., and one, or two or more of these agents can be used. Particularly preferred reducing agents are ascorbic acid and erythorbic acid which makes it possible to start the polymerization at a temperature in the range of from 0° C. to 30° C. in combination with an oxidizing agent.

The reducing agent is generally used in an amount of from 0.000001 to 1 g, preferably from 0.00001 to 0.1 g, and more preferably from 0.00001 to 0.01, per mol of the monomer component (A).

In the present invention, a thermal polymerization initiator can be used depending upon the selected reaction temperature and the type of the selected monomer component (A). The thermal polymerization initiator is preferably soluble in water or the aqueous solution (D) containing the monomer component (A), the compound (B) and the compound (C). Examples of the thermal polymerization initiator include azo initiators such as 2,2-azobis-amidinopropane dihydrochloride, 4,4-butylazo-cyanovaleric acid, and 2,2'-azobis(isobutylonitrile). These thermal polymerization initiators can be used singly or in combination of two or more of them together with the redox polymerization initiator if desired. Preferred thermal polymerization initiators include 2,2'-azobis-amidinopropane dihydrochloride.

The thermal polymerization initiator used in the present invention is preferably used in an amount of from 0.00001 to 10 g, preferably, from 0.001 to 1 g, per mol of the monomer component (A).

It is possible to use an appropriate combination of the redox polymerization initiator and the thermal polymerization initiator by taking the reactivity of these initiators into consideration. The most preferred combination is that of hydrogen peroxide, ascorbic acid, sodium persulfate, and 2,2-azobis-amidinopropane dihydrochloride because this combination exhibits excellent polymerization initiating function and polymerizability at a low temperature, resulting in a water-absorbing resin having a small amount of water-soluble content.

The total amount of these polymerization initiators used is generally in the range of from 0.000001 to 10 g, preferably from 0.00001 to 5 g, and more preferably from 0.001 to 1 g, per mol of the monomer component (A).

A conventionally known process for initiating the polymerization may be used in combination with the process for initiating the polymerization according to the present invention, as long as the polymerization is initiated with a redox polymerization initiator. Examples of such a process include a process of radiation with a radioactive ray, an electron beam, a ultraviolet ray, etc.

The polymerization initiating temperature in the process for producing a water-absorbing resin according to the present invention may differ depending upon the type of initiators used. The polymerization is generally initiated at a temperature in the range of from 0° to 30° C., preferably from 0° to 20° C. At a temperature below 0° C., a long period of time may be required before initiating the polymerization. At a temperature higher than 30° C., a basic molecular weight of the resulting water-absorbing resin tends to decrease and the amount of a water-soluble content in the resin tends to increase.

In the process of the present invention, the maximum reaction temperature is in the range of from 60° to 100° C. The term "maximum reaction temperature" as used herein means a maximum temperature of the reaction system reached by generating polymerization heat. If the maximum reaction temperature is lower than 60° C., a large amount of monomers remains unreacted. If the maximum reaction temperature is higher than 100° C., the reaction cannot be controlled due to boiling during the reaction and an amount of water-soluble content in the resulting water-absorbing resin increases.

A polymerization vessel used for polymerizing the aqueous solution (D) used in the present invention is not particularly limited. When the aqueous solution (D) is polymerized in a vessel having a plurality of revolving stirrer shaft, a vessel which is capable of providing a shearing force which is capable of finely dividing the hydrogel produced as a result of the polymerization by rotation of the revolving stirrer shaft is preferred since the maximum reaction temperature can be easily controlled by removing the heat. As such vessels, a double-arm kneader is particularly preferred. The blade equipped with revolving stirrer shaft of the double-arm kneader which can be used include a sigma type, an S type, a Banbury type, a fish-tail type, a masticator type, etc.

In the process of the present invention, the concentration of the monomer component (A) in the aqueous solution (D) containing the monomer component (A), the compound (B) and the compound (C) is not particularly limited, but, in consideration of easiness for controlling the polymerization reaction and the economy, the concentration of the monomer component (A) is preferably in the range of from 15 to 70% by weight, more preferably in the range of from 20 to 50% by weight.

The aqueous solution (D) used in the present invention may, if desired, contain other monomers than the monomer component (A). These monomers is not particularly limited, but those which are water-soluble and/or soluble in unsaturated carboxylic acids are preferred.

Examples of other monomers include (meth)acrylic acid esters such as hydroxyethyl (meth)acrylate, methoxyethyl (meth)acrylate, hydroxypropyl (meth)acrylate, polyethylene glycol mono(meth)acrylate, polypropylene glycol mono (meth)acrylate, methoxy polyethylene glycol mono(meth) acrylate, methoxy polypropylene glycol mono(meth) acrylate, methyl (meth)acrylate and ethyl (meth)acrylate; unsaturated sulfonic acids and salts thereof such as 2-acrylamido-2-methylpropanesulfonic acid, vinylsulfonic acid, (meth)acrylsulfonic acid, styrenesulfonic acid, sulfoethyl (meth)acrylate, sulfopropyl (meth)acrylate and vinyltoluenesulfonic acid; unsaturated amine compounds and salts thereof such as N,N-dimethylaminoethyl (meth) acrylate and N,N-diethylaminoethyl (meth)acrylate; unsaturated amides such as (meth)acrylamide, N-hexyl (meth) acrylamide, N-methylol (meth)acrylamide and N,N-dimethyl (meth)acrylamide; styrene or derivatives thereof such as styrene, -methylstyrene, o-methylstyrene and p-methylstyrene; (meth)acrylonitrile and vinyl acetate. These monomers may be used singly or in combination of two or more of them. These monomers may be used, if desired, in an amount of 50% by weight or less, preferably 40% by weight or less, based on the amount of the monomer component (A).

Various polymerization systems can be employed in the process for producing the water-absorbing resin according to the present invention, and conventional methods for obtaining water-absorbing resins such as a reverse phase suspension polymerization method, an aqueous solution polymerization method, and a spray polymerization method can be used. An aqueous solution of monomers supported on a fibrous substrate can be polymerized. A preferred method is an aqueous solution polymerization method, and, in particular, a method for polymerization while finely dividing a hydrogel by shearing force is preferred from the standpoint of removal of heat.

As solvents for the polymerization used in the present invention, the use of only water is preferred, but, if necessary, a hydrophilic organic solvent such as methanol, ethanol, isopropanol, acetone, dimethylformamide and dimethyl sulfoxide may be added to water. Further, a chelating agent may be added to water.

The water-absorbing resin obtained by the process according to the present invention may be used as an absorbent, a water-retention agent, etc. in the form of a hydrogel. When removal of water by drying is preferred from the standpoint of handling, it may be used after appropriate drying. In this case, the water content of the water-absorbing absorbing resin is generally 70% or less, preferably 10% or less. The drying temperature can be in the range of from 90° to 250° C., preferably 100° to 180° C. An ordinary dryer, such as a hot air dryer, a reduced pressure dryer, etc. can be used. A drying temperature of 90° C. or below may not be economical since, for example, a high degree of reduced pressure is required for improving the productivity. A drying temperature of 250° C. or above may cause discoloration, etc. of the water-absorbing resin.

The water-absorbing resin obtained after drying in the above manner is used as it is in the form of coarse particles, or in the form of powder by pulverization.

If necessary, the water-absorbing resin obtained by the process of the present invention may be secondarily crosslinked on the surface thereof by a polyhydric alcohol, a polyvalent epoxy compound, a polyvalent glycidyl compound, a polyvalent azilidine compound, a polyvalent amine compound, a polyvalent isocyanate compound, a glyoxal, a polyvalent metal salt, a silane coupling agent, an alkylene carbonate, etc. The secondary crosslinking may be carried out at least one occasions selected from before drying, simultaneously with drying, and after drying.

The water-absorbing resin obtained by the process of the present invention may contain inorganic fine particles such as titanium oxide, silicon oxide and activated carbon; organic fine particles such as polymethyl methacrylate; hydrophilic fibers such as pulp; synthetic fibers such as a polyethylene fiber and a polypropylene fiber; etc. which are added during the production steps or after the production of the resin.

The present invention also relates to a water-absorbing resin.

The water-absorbing resin of the present invention has a degree of reduction in absorption magnification of from 1 to 16, and an absorption magnification under pressure of from 20 to 40.

A water-absorbing resin having a degree of reduction in absorption magnification of more than 16 drains an electrolytic solution that has been once absorbed with the lapse of time, and therefore is not preferred since it results in practical problems. For example, if a water-absorbing resin having such a high degree of reduction in absorption magnification is used in a diaper, urine that has been once absorbed is drained from the water-absorbing resin with the lapse of time, which will give an unpleasant feeling to a person using the diaper, or will cause leakage of urine since no further urine is absorbed by the water-absorbing resin.

A water-absorbing resin having a degree of reduction in absorption magnification is less than 1, particularly a water-absorbing resin having an absorption magnification after 3 hours larger than that after 10 minutes, is not preferred because it generally has a low absorbing rate and thus requires a long period of time until it reaches the saturated absorption.

The degree of reduction in absorption magnification of the water-absorbing resin of the present invention is preferably from 1 to 12.

A water-absorbing resin having an absorption magnification under pressure of less than 20 is not preferred because the absorbing properties of such a water-absorbing resin is deteriorated when it is applied to practical use, in which the water-absorbing resin used under pressure. For example, if a water-absorbing resin having a low absorption magnification under pressure is used in a disposable diaper, the water-absorbing resin receives pressure by a person using the diaper and cannot exhibit sufficient absorbing properties, i.e., cannot sufficiently absorb urine.

The absorption magnification under pressure of the water-absorbing resin of the present invention is preferably 23 to 40.

A production process of the water-absorbing resin of the present invention is not particularly limited if the resulting water-absorbing resin satisfies the requirements in the degree of reduction in absorption magnification and the absorption magnification under pressure, and any of conventional processes may be employed. The water-absorbing resin of the present invention is preferably produced by the production process according to the present invention.

The present invention also relates to a water-absorbing article.

The water-absorbing article according to the present invention comprises a water-absorbing resin having a degree of reduction in absorption magnification of from 1 to 16, and an absorption magnification under pressure of from 20 to 40.

The form of the water-absorbing article of the present invention is not particularly limited and may be in the form of sheet, mass or the like.

The water-absorbing article of the present invention is not limited in other constituting components, as long as it comprises the above water-absorbing resin. For example, the water-absorbing article may further comprise a water-permeable sheet material, a water-impermeable sheet material, crushed pulp, tissue paper, a rubber material, etc. Examples of the water-absorbing article include one in which the above water-absorbing resin is placed in a bag which comprises at least one side thereof a water-permeable sheet.

The water-absorbing article of the present invention can absorb various liquids including body fluids such as urine and blood, liquids from food such as meat, fish, fruit and vegetables, ground water, brine, rainwater, etc., and thus can be applied to various products such as diapers, sanitary goods, freshness-maintaining agents, soil water-retaining retaining agents, sealing materials, dew condensation preventing agents.

The water-absorbing article of the present invention is particularly preferably applied to a disposable diaper because the degree of reduction in absorption magnification to urine, which is an electrolytic solution, is low, and the absorbing properties under pressure, i.e., load of the weight of a human body, is excellent.

The present invention is further illustrated in more detail by the following Examples and Comparative Examples, but the present invention should not be construed as being limited to these examples.

The absorption capability, the amount of water-soluble content, the degree of reduction in absorption magnification, and the absorption magnification under pressure in Examples and Comparative Examples were measured in the following procedures. (1) Absorption capability Into a container having a circle bottom having a diameter of 9.5 cm, 16 sheets of toilet paper each having a rectangular form of 7.5 cm×5.7 cm were placed parallel to the bottom, and 20 g of an artificial urine I (an aqueous solution containing 1.9% of urea, 0.8% of sodium chloride, 0.1% of magnesium sulfate, and 0.1% of calcium chloride) at 25° C. was poured into the container. A (g) (about 1 g) of the water-absorbing resin was placed at the center of the toilet paper and was allowed to absorb and swell for 10 minutes. The weight (B (g)) of the absorbed and swollen water-absorbing resin was measured, and the absorbing capability was calculated by the following equation:

Absorbing capability $(g/g)=B(g)/A(g)$ (2) Amount of water-soluble content

C (g) (about 0.5 g) of the water-absorbing resin was dispersed in 1,000 g of deionized water, and, after stirring for 16 hours, the dispersion was filtered through a filter paper and the weight of the solid content in the filtrate was measured (D (g)). The amount of the water-soluble content was calculated by the following equation:

Amount of water-soluble content $(wt\%)=(D(g)/C(g))\times 100$ (3) Degree of reduction in absorption magnification E (g) (about 0.2 g) of a water-absorbing resin to be measured was placed uniformly in a bag made of nonwoven cloth (40×150 mm), and immersed in an artificial urine I (an aqueous solution containing 1.9% of urea, 0.8% of sodium chloride, 0.1% of magnesium sulfate, and 0.1% of calcium chloride) at 25° C. for a prescribed period of time. After the bag was taken out from the artificial urine I, the artificial urine I was naturally drained for 5 second in the air and for further 10 seconds on 24 sheets of toilet paper each having a rectangular form of 5.0 cm×5.7 cm, and the weight (F (g)) of the bag containing the water-absorbing resin was measured. The same procedures as above were conducted by using the same nonwoven cloth bag but using no water-absorbing resin, and the weight (G (g)) of the bag was measured. The absorption magnification at the prescribed period of time was calculated by the following equation:

Absorption magnification $(g/g)=(F(g)-G(g))/E(g)$

The degree of reduction in absorption magnification was calculated by the following equation:

Degree of reduction in absorption magnification $(g/g)$=Absorption magnification after 10 minutes $(g/g)$–Absorption magnification after 3 hours $(g/g)$ (4) Absorption magnification under pressure The absorption magnification under pressure was measured by using an apparatus shown in FIG. 1. An artificial urine II 3 (an aqueous solution containing 2.0% of potassium chloride, 2.0% of anhydrous sodium sulfate, 0.85% of ammonium dihydrogenphosphate, 0.15% of ammonium dihydrogenphosphate, 0.25% of potassium chloride dihydrate, and 0.5% of magnesium chloride hexahydrate) at 25° C. was placed in a vessel 4 equipped with an air inlet pipe 2, which was placed on a balance 1. The interior of the vessel 4 was connected to a reverse funnel 6 through a connecting pipe 5. A glass filter 7 was fixed at the top of the reverse funnel 6, while the top end of the glass filter 7 and the bottom end 8 of the air inlet pipe 2 were placed at the same height. A cylinder 13 (inner diameter: 6.0 cm) having a stainless steel mesh bottom 12 containing a water-absorbing resin 11 (0.9 g) having placed thereon a weight 10 (pressure: 0.70 psi) was placed on the glass filter 7. The weight of the artificial urine II 3 that were absorbed by the water-absorbing resin 11 after 60 minutes was divided by 0.9 to result absorption magnification under pressure (g/g).

EXAMPLE 1

A jacketed 13-liter-content stainless steel double-arm kneader equipped with two sigma-type blades having a rotating diameter of 120 mm was charged with 6,538 g of an aqueous solution (D) containing 2,168 g of a monomer component (A) composed of 35 mol% of acrylic acid and 65 mol% of sodium acrylate; 24.5 g of polyethylene glycol diacrylate (an average molecular weight: 478) as a compound (B); 13.1 g of ethylene glycol diglycidyl ether as a compound (C) and 4,332.4 g of deionized water. The resulting aqueous solution (D) was degassed and the reaction system was replaced with a nitrogen gas.

Water at 20° C. was passed through the jacket to control the temperature of the vessel. 12.56 g of a 10 wt% aqueous solution of 2,2-azobis-2-amidinopropane dihydrochloride, 0.88 g of a 1 wt% aqueous solution of L-ascorbic acid, 12.56 g of a 10 wt% aqueous solution of sodium persulfate, and 5.6 g of a 0.35 wt% aqueous solution of hydrogen peroxide as initiators were added to the reaction system. The initial polymerization temperature was controlled to 20° C. After initiation of the polymerization reaction, the reaction was further continued for 35 minutes. During the polymerization, the revolving shaft was suitably rotated to obtain finely divided hydrogel. The maximum reaction temperature was 75° C. The resulting hydrogel was dried with hot air on a metal mesh at a temperature condition of 150° C. for 90 minutes. The resulting dried material was pulverized with a hammer-mill to obtain a water-absorbing resin in the form of powder that could pass through a mesh of 850 μm. The properties of the resulting water-absorbing resin are shown in Table 1.

EXAMPLE 2

A water-absorbing resin was obtained in the same manner as in Example 1 except for changing the amount of ethylene glycol diglycidyl ether in Example 1 to 21.8 g. The properties of the resulting water-absorbing resin are shown in Table 1.

EXAMPLE 3

A water-absorbing resin was obtained in the same manner as in Example 1 except for changing the amount of ethylene glycol diglycidyl ether in Example 1 to 4.4 g. The properties of the resulting water-absorbing resin are shown in Table 1.

EXAMPLE 4

A water-absorbing resin was obtained in the same manner as in Example 1 except for changing the amounts of ethylene glycol diacrylate and ethylene glycol diglycidyl ether in Example 1 to 12.3 g and 21.8 g, respectively. The properties of the resulting water-absorbing resin are shown in Table 1.

EXAMPLE 5

A water-absorbing resin was obtained in the same manner as in Example 1 except for changing the amount of ethylene glycol diglycidyl ether in Example 1 to 2.2 g. The properties of the resulting water-absorbing resin are shown in Table 1.

EXAMPLE 6

A water-absorbing resin was obtained in the same manner as in Example 1 except for changing the amount of polyethylene glycol diacrylate and ethylene glycol diglycidyl ether in Example 1 to 12.3 g and 4.4 g, respectively. The properties of the resulting water-absorbing resin are shown in Table 1.

Comparative Example 1

A water-absorbing resin was obtained in the same manner as in Example 1 except for changing the amount of polyethylene glycol diacrylate in Example 1 to 61.2 g and ethylene glycol diglycidyl ether was not used. The properties of the resulting water-absorbing resin are shown in Table 1.

Comparative Example 2

A water-absorbing resin was tried to obtain in the same manner in Example 1 except that polyethylene glycol diacrylate was not used and the amount of ethylene glycol diglycidyl ether in Example 1 was changed to 21.8 g, but dividing of the hydrogel could not proceed after initiation of the polymerization, and the hydrogel bumped. The properties of the resulting water-absorbing resin are shown in Table 1.

Comparative Example 3

A water-absorbing resin was obtained in the same manner as in Example 1 except that ethylene glycol diglycidyl ether was not used. The properties of the resulting water-absorbing resin are shown in Table 1.

Comparative Example 4

A water-absorbing resin was tried to obtain in the same manner as in Example 1 except that L-ascorbic acid and hydrogen peroxide were not used and the amount of the 10% aqueous solution of 2,2'-azobis-2-amidinopropane dihydrochloride in Example 1 was changed to 25 g, but polymerization did not start.

The temperature of the jacket was then elevated to 50° C., and a temperature at which the reaction started was 46° C. The maximum reaction temperature was 115° C. The properties of the resulting water-absorbing resin are shown in Table 1.

Comparative Example 5

A water-absorbing resin was obtained in the same manner as in Example 1 except that water at 0° C. was passed through the jacket after initiation of the polymerization. The maximum reaction temperature was 51° C. The properties of the resulting water-absorbing resin are shown in Table 1.

EXAMPLE 7

The water-absorbing resin obtained in Example 1 was designated Water-absorbing resin 1; that obtained in Example 2 was designated Water-absorbing resin 2; and that obtained in Example 3 was designated Water-absorbing resin 3. The degree of reduction in absorption magnification and the absorption magnification under pressure of Water-absorbing resins 1 to 3 were measured. The results are shown in Table 2.

Comparative Example 6

Water-absorbing resins were taken out from commercially available disposal diapers. A water-absorbing resin taken out from "Huggies Ultratrim Step 3" made by Kimbary Clerk was designated Water-absorbing resin 4; and that taken out from "Pampers Phases Walker 2" made by P & G was designated Water-absorbing resin 5. The degree of reduction in absorption magnification and the absorption magnification under pressure of Water-absorbing resins 4 and 5 were measured. The results are shown in Table 2.

Comparative Example 7

A water-absorbing resin for waterproofing material for cables was produced in the manner described in Example 1 of JP-A-4-363383. A 500 -ml cylindrical separable flask was charged with 31.3 g of sodium acrylate, 55.2 g of acrylic amide, 0.12 g of N,N-methylenebisacrylic amide, and 164.9 g of water, to produce a uniform solution.

After replacing the reaction system by nitrogen, the flask was heated to 25° C. over a water bath, and then 1.94 g of a 20% aqueous solution of sodium persulfate and 1.94 g of a 2% aqueous solution of L-ascorbic acid were added thereto, to initiate polymerization without stirring. The reaction system generated heat after starting the polymerization, and the temperature of the reaction system was increased to 90° C. after 40 minutes. After the increase of the temperature was stopped, the temperature of the water bath was increased to 90° C., and the reaction system was aged for 40 minutes. The resulting polymer was divided into small pieces, dried at 160° C. for 3 hours, and then crushed to

TABLE I

| | Amount of compound (B)[*1] | Amount of compound (C)[*1] | (B)/(C)[*2] | Absorption capability (g/g) | Amount of water-soluble content (wt %) | Maximum reaction temperature (°C.) |
|---|---|---|---|---|---|---|
| Example 1 | 0.0020 | 0.0030 | 0.67 | 14.7 | 0.6 | 75 |
| Example 2 | 0.0020 | 0.0050 | 0.40 | 14.4 | 0.5 | 76 |
| Example 3 | 0.0020 | 0.0010 | 2.00 | 14.7 | 0.8 | 74 |
| Example 4 | 0.0010 | 0.0050 | 0.20 | 14.1 | 0.4 | 77 |
| Example 5 | 0.0020 | 0.0005 | 4.00 | 15.0 | 1.0 | 74 |
| Example 6 | 0.0010 | 0.0010 | 1.00 | 15.0 | 1.2 | 74 |
| Comparative Example 1 | 0.0050 | 0.0000 | — | 15.2 | 1.5 | 77 |
| Comparative Example 2 | 0.0000 | 0.0050 | 0.00 | 14.5 | 3.6 | 110 |
| Comparative Example 3 | 0.0020 | 0.0000 | — | 15.4 | 2.2 | 74 |
| Comparative Example 4 | 0.0020 | 0.0030 | 0.67 | 14.2 | 5.8 | 115 |
| Comparative Example 5 | 0.0020 | 0.0030 | 0.67 | 12.9 | 3.8 | 51 |

Note:
[*1] Molar ratio to the monomer component (A)
[*2] Molar ratio of the compound (B) to the compound (C)

obtain a water-absorbing resin, which was designated Water-absorbing resin 6. The degree of reduction in absorption magnification and the absorption magnification under pressure of Water-absorbing resin 6 were measured. The results are shown in Table 2.

TABLE 2

|  | Degree of reduction in adsorption magnification (g/g) | Absorption magnification under pressure (g/g) | Absorption magnification after 10 minutes (g/g) |
| --- | --- | --- | --- |
| Example 7 |  |  |  |
| Water-absorbing resin 1 | 10.8 | 29.5 | 20.5 |
| Water-absorbing resin 2 | 9.3 | 26.3 | 18.6 |
| Water-absorbing resin 3 | 14.8 | 25.6 | 24.8 |
| Comparative Example 6 |  |  |  |
| Water-absorbing resin 4 | 16.6 | 8.6 | 26.6 |
| Water-absorbing resin 5 | 18.4 | 29.7 | 27.7 |
| Comparative Example 7 |  |  |  |
| Water-absorbing resin 6 | −1.1 | 5.1 | 23.7 |

EXAMPLE 8

Water-absorbing articles were prepared by using Water-absorbing resins 1 to 3. An artificial urine was poured onto the water-absorbing article, and after the prescribed period of time, the touch feeling of the water-absorbing articles was examined.

The water-absorbing articles were prepared in the following manner: (300/(absorption magnification after 10 minutes)) g of the water-absorbing resin and 10 g of crushed pulp was mixed in a mixer in a dry condition. A web (10 cm×30 cm) was prepared from the resulting mixture by using a batch-type air-web-manufacturer. The resulting web was sandwiched with two sheets of tissue paper having a unit weight of 0.001 g/cm² and then pressed to produce a water-absorbing article according to the present invention.

100 g of the artificial urine I at 25° C. was poured onto the center of the water-absorbing article, and a load of 0.3 psi was placed on the water-absorbing article. After the prescribed period of time, the load was removed, and the touch feeling of the water-absorbing article was examined by a panel composed of 10 persons. The evaluation was decided by majority to the following three grades:

A: Dry state

B: Moist state

C: Wet state

The hand feeling of the water-absorbing articles using Water-absorbing resins 1 to 3 after 10 minutes or 3 hours was examined. The results are shown in Table 3.

Comparative Example 8

The hand feeling of the water-absorbing articles using Water-absorbing resins 4 to 6 after 10 minutes or 3 hours was examined in the same manner as in Example 8. The results are shown in Table 3.

TABLE 3

|  | Touch feeling after 10 minutes | Touch feeling after 3 hours |
| --- | --- | --- |
| Example 8 |  |  |
| Water-absorbing resin 1 | A | A |
| Water-absorbing resin 2 | A | A |
| Water-absorbing resin 3 | A | B |
| Comparative Example 8 |  |  |
| Water absorbing resin 4 | C | C |
| Water-absorbing resin 5 | A | C |
| Water-absorbing resin 6 | C | C |

The water-absorbing resin obtained by the process of the present invention has a sufficient absorption capability and a small amount of water-soluble content, resulting in a high safety. When the water-absorbing resin obtained by the process of the present invention is used as an absorbent in absorbing articles such as diapers or sanitary goods, products having a good absorbing properties can be provided.

The water-absorbing resin of the present invention has a small amount of water-soluble content, a high salt resistance, and excellent absorbing properties under pressure. The water-absorbing resin of the present invention having a low degree of reduction in absorption magnification and a high absorption magnification under pressure can retain an electrolytic solution once absorbed, and the absorption can be carried out under pressure. For example, disposable diapers, soil water-retaining agents, and sealing materials for brine require to absorb and retain an electrolytic solution under pressure, and therefore the water-absorbing resin of the present invention having a low degree of reduction in absorption magnification and a high absorption magnification under pressure can advantageously used for these purposes.

The water-absorbing article of the present invention is excellent in absorbing properties to an electrolytic solution. The water-absorbing article of the present invention has a reduced change in absorbing properties after absorption, which has been a problem in coventional water-absorbing articles. When the water-absorbing article is applied to a diaper, the diaper is of good feeling upon use since the absorbing properties do not change after absorbing an electrolytic solution such as urine.

While the invention has been described in detail and with reference to specific examples thereof, it will be apparent to one skilled in the art that various changes and modifications can be made therein without departing from the spirit and scope thereof.

What is claimed is:

1. A water-absorbing resin having a degree of reduction in absorption magnification of from 1 to 16, and an absorption magnification under pressure of from 20 to 40.

2. A water-absorbing resin having a degree of reduction in absorption magnification of from 1 to 16, and an absorption magnification under pressure of from 20 to 40, said water-absorption resin being produced by a process, which comprises polymerizing (D) an aqueous solution comprising (A) at least one monomer component selected from the group consisting of an unsaturated carboxylic acid and salts thereof; (B) a compound having two or more unsaturated groups in a molecule and being capable of polymerizing by reacting with the unsaturated bonds in monomer component (A); and (C) a compound having zero or one unsaturated group which is capable of polymerizing by reacting With the unsaturated bonds in monomer component (A) and having two or more functional groups which are capable of reacting with carboxyl groups in a molecule, said polymerization being conducted in such a manner that the following conditions (a) to (c) are simultaneously satisfied:

(a) the molar ratio (B)/(C) being in the range of from $2 \times 10^{-3}$, (b) said polymerization being initiated by a redox polymerization initiator, and (c) the maximum reaction temperature being in the range of from 60° to 100° C.

3. A water-absorbing resin as claimed in claim 2, wherein said water-absorbing resin comprises a repeating unit derived from (A) at least one monomer component selected from the group consisting of an unsaturated carboxylic acid and salts thereof; a repeating unit derived from (B) a compound having two or more unsaturated groups in a molecule and being capable of polymerizing by reacting with the unsaturated bonds in monomer component (A); and a repeating unit derived from (C) a compound having zero or one unsaturated group which is capable of polymerizing by reacting with the unsaturated bonds in monomer component (A) and having two or more functional groups which are capable of reacting with carboxyl groups in a molecule.

4. A water-absorbing resin as claimed in claim 2, wherein said water-absorbing resin comprises a repeating unit derived from (A) at least one monomer component selected from the group consisting of an unsaturated carboxylic acid and salts thereof; a repeating unit derived from (B) a compound having two or more unsaturated groups in a molecule and being capable of polymerizing by reacting with the unsaturated bonds in monomer component (A); and a repeating unit derived from (C) a compound having zero or one unsaturated group which is capable of polymerizing by reacting with the unsaturated bonds in monomer component (A) and having two or more functional groups which are capable of reacting with carboxyl groups in a molecule.

5. A water-absorbing resin as claimed in claim 2, wherein the molar ratio (B)/(A) is in the range of from $1 \times 10^{-4}$ to $3 \times 10^{-3}$.

6. A water-absorbing resin as claimed in claim 2, wherein the molar ratio (C)/(A) is in the range of from $5 \times 10^{-5}$ to $1 \times 10^{-2}$.

7. A water-absorbing resin as claimed in claim 2, wherein said polymerization is conducted in such a manner that the following conditions (d) to (f) are simultaneously satisfied:

(d) the molar ratio (B)/(C) being in the range of from 0.01 to 30, (e) the molar ratio (B)/(A) being in the range of from $1 \times 10^{-4}$ to $3 \times 10^{-3}$, and (f) the molar ratio (C)/(A) being in the range of from $1 \times 10^{-4}$ to $1 \times 10^{-2}$.

8. A water-absorbing resin as claimed in any one of claims 2 and 5 to 7, wherein said functional group capable of reacting with a carboxyl group in (C) is an epoxyl group.

9. A water-absorbing resin as claimed in any one of claims 2 and 5 to 7, wherein said monomer component (A) is at least one selected from the group consisting of acrylic acid and an alkali metal salt thereof.

10. A water-absorbing resin as claimed in any one of claims 2 and 5 to 7, wherein said redox polymerization initiator is an initiator system comprising a reducing agent selected from the group consisting of ascorbic acid, erythorbic acid, and metallic salts of these.

11. A water-absorbing resin as claimed in claim 10, wherein said polymerization is initiated at a temperature in the range of from 0° to 30° C.

12. A water-absorbing resin as claimed in claim 2, wherein the process further comprising drying after said polymerization.

13. A water-absorbing resin as claimed in claim 12, wherein said drying is conducted at a temperature in the range of from 90° to 250° C.

14. A water-absorbing resin as claimed in any one of claims 2, 5 to 7, and 12, wherein said polymerization of (D) is a radical aqueous polymerization conducted in a vessel capable of finely dividing a hydrogel produced as a result of said polymerization by a shearing force caused by revolution of a plurality of revolving stirring shaft.

15. A water-absorbing resin as claimed in claim 14, wherein said vessel is a double-arm kneader.

16. A water-absorbing article comprising a water-absorbing resin having a degree of reduction in absorption magnification of from 1 to 16, and an absorption magnification under pressure of from 20 to 40.

17. A water-absorbing article as claimed in claim 16, wherein said water-absorbing article is a diaper.

18. A water-absorbing article comprising a water-absorbing resin having a degree of reduction in absorption magnification of from 1 to 16, and an absorption magnification under pressure of from 20 to 40, said water-absorption resin being produced by a process, which comprises polymerizing (D) an aqueous solution comprising (A) at least one monomer component selected from the group consisting of an unsaturated carboxylic acid and salts thereof; (B) a compound having two or more unsaturated groups in a molecule and being capable of polymerizing by reacting with the unsaturated bonds in monomer component (A); and (C) a compound having zero or on. unsaturated group which is capable of polymerizing by reacting with the unsaturated bonds in monomer component (A) and having two or more functional groups which are capable of reacting with carboxyl groups in a molecule, said polymerization being conducted in such a manner that the following conditions (a) to (c) are simultaneously satisfied:

(a) the molar ratio (B)/(C) being in the range of from $2 \times 10^{-3}$, (b) said polymerization being initiated by a redox polymerization initiator, and (c) the maximum reaction temperature being in the range of from 60° to 100° C.

19. A water-absorbing article as claimed in claim 18, wherein said water-absorbing article is a diaper.

* * * * *